(12) United States Patent
Traxel et al.

(10) Patent No.: US 6,694,168 B2
(45) Date of Patent: Feb. 17, 2004

(54) FIDUCIAL MATCHING USING FIDUCIAL IMPLANTS

(75) Inventors: Doris Traxel, Basel (CH); Roger Berger, Büren (CH)

(73) Assignee: Synthes (U.S.A.), Paoli, PA (US)

(*) Notice: Subject to any disclaimer, the term of this patent is extended or adjusted under 35 U.S.C. 154(b) by 111 days.

(21) Appl. No.: 09/741,198

(22) Filed: Dec. 21, 2000

(65) Prior Publication Data

US 2001/0010004 A1 Jul. 26, 2001

Related U.S. Application Data

(63) Continuation of application No. PCT/CH98/00269, filed on Jun. 22, 1998.

(51) Int. Cl.$^7$ .................................................. A61B 5/05
(52) U.S. Cl. ........................ 600/426; 600/425; 600/407; 600/300
(58) Field of Search .............................. 600/407, 414, 600/425, 426, 417, 429; 606/53, 60, 96

(56) References Cited

U.S. PATENT DOCUMENTS

| | | | |
|---|---|---|---|
| 3,821,469 A | 6/1974 | Whetstone et al. | 178/18 |
| 3,983,474 A | 9/1976 | Kuipers | 324/43 |
| 4,058,114 A | 11/1977 | Soldner | 128/2 |
| 4,146,924 A | 3/1979 | Birk et al. | 364/513 |
| 4,182,312 A | 1/1980 | Mushabac | 433/68 |
| 4,204,225 A | 5/1980 | Mistretta | 358/111 |
| 4,209,254 A | 6/1980 | Reymond et al. | 356/152 |
| 4,262,306 A | 4/1981 | Renner | 358/93 |
| 4,341,220 A | 7/1982 | Perry | 128/630 |
| 4,358,856 A | 11/1982 | Stivender et al. | 378/167 |
| 4,396,945 A | 8/1983 | DiMatteo et al. | 358/107 |
| 4,418,422 A | 11/1983 | Richter et al. | 378/205 |
| 4,419,012 A | 12/1983 | Stephenson et al. | 356/141 |
| 4,437,161 A | 3/1984 | Anderson | 364/414 |
| 4,457,311 A | 7/1984 | Sorenson et al. | 128/660 |

(List continued on next page.)

FOREIGN PATENT DOCUMENTS

| | | |
|---|---|---|
| DE | 195 06 197 A1 | 5/1996 |
| DE | 195 36 180 A1 | 6/1997 |
| DE | 297 04 393 U1 | 7/1997 |
| EP | 0 062 941 A1 | 10/1982 |
| EP | 0 326 768 A2 | 8/1989 |
| EP | 0 591 712 A1 | 4/1994 |
| EP | 0 647 428 A2 | 4/1995 |
| EP | 0 832 609 A2 | 4/1998 |
| GB | 2 094 590 A | 9/1982 |
| WO | WO 90/05494 | 5/1990 |
| WO | WO 91/07726 | 5/1991 |
| WO | WO 94/23647 | 10/1994 |
| WO | WO 94/24933 | 11/1994 |
| WO | WO 95/15729 | 6/1995 |
| WO | WO 95/31148 | 11/1995 |
| WO | WO 96/11624 | 4/1996 |
| WO | WO 97/29685 | 8/1997 |
| WO | WO 97/29709 | 8/1997 |
| WO | WO 97/47240 | 12/1997 |

OTHER PUBLICATIONS

Nolte et al., "Clinical Evaluation of a System for Precision Enhancement in Spine Surgery," *Clinical Biomechanics*, vol. 10, No. 6, pp. 293–303 (1995).

*Primary Examiner*—Henry Bennett
*Assistant Examiner*—Nihir Patel
(74) *Attorney, Agent, or Firm*—Pennie & Edmonds LLP

(57) ABSTRACT

The invention relates to a device and method for referencing reference points of a fiducial implant. The fiducial implant and pointer are configured to removably and reproducibly mate to provide a known spatial relationship between the reference points and the pointer. A position finder is used to determine the position of the pointer in three-dimensional space to allow the position of each reference point in three dimensional space to be determined.

25 Claims, 2 Drawing Sheets

U.S. PATENT DOCUMENTS

| | | | | |
|---|---|---|---|---|
| 4,465,069 | A | 8/1984 | Barbier et al. | 128/303 |
| 4,473,074 | A | 9/1984 | Vassiliadis | 128/303.1 |
| 4,485,815 | A | 12/1984 | Amplatz et al. | 128/329 |
| 4,543,959 | A | 10/1985 | Seponen | 128/653 |
| 4,571,834 | A | 2/1986 | Fraser et al. | 33/1 |
| 4,583,538 | A | 4/1986 | Onik et al. | 128/303 |
| 4,592,352 | A | 6/1986 | Patil | 128/303 |
| 4,598,368 | A | 7/1986 | Umemura | 364/414 |
| 4,602,622 | A | 7/1986 | Bär et al. | 128/303 |
| 4,613,866 | A | 9/1986 | Blood | 343/448 |
| 4,613,942 | A | 9/1986 | Chen | 364/513 |
| 4,618,978 | A | 10/1986 | Cosman | 378/164 |
| 4,638,798 | A | 1/1987 | Shelden et al. | 128/303 |
| 4,649,504 | A | 3/1987 | Krouglicof et al. | 364/559 |
| 4,651,732 | A | 3/1987 | Frederick | 128/303 |
| 4,670,781 | A | 6/1987 | Aubert et al. | 358/93 |
| 4,672,564 | A | 6/1987 | Egli et al. | 364/559 |
| 4,674,057 | A | 6/1987 | Caughman et al. | 364/513 |
| 4,729,098 | A | 3/1988 | Cline et al. | 364/414 |
| 4,733,661 | A | 3/1988 | Palestrant | 128/303 |
| 4,733,969 | A | 3/1988 | Case et al. | 356/375 |
| 4,737,032 | A | 4/1988 | Addleman et al. | 356/376 |
| 4,742,815 | A | 5/1988 | Ninan et al. | 128/4 |
| 4,743,770 | A | 5/1988 | Lee | 250/560 |
| 4,743,771 | A | 5/1988 | Sacks et al. | 250/560 |
| 4,745,290 | A | 5/1988 | Frankel et al. | 250/360 |
| 4,750,487 | A | 6/1988 | Zanetti | 128/303 |
| 4,753,528 | A | 6/1988 | Hines et al. | 356/1 |
| 4,760,851 | A | 8/1988 | Fraser et al. | 128/774 |
| 4,761,072 | A | 8/1988 | Pryor | 356/1 |
| 4,762,016 | A | 8/1988 | Stoughton et al. | 74/479 |
| 4,763,652 | A | 8/1988 | Brisson et al. | 128/328 |
| 4,764,016 | A | 8/1988 | Johansson | 356/371 |
| 4,776,749 | A | 10/1988 | Wanzenberg et al. | 414/680 |
| 4,779,212 | A | 10/1988 | Levy | 364/562 |
| 4,782,239 | A | 11/1988 | Hirose et al. | 250/561 |
| 4,791,934 | A | 12/1988 | Brunnett | 128/653 |
| 4,793,355 | A | 12/1988 | Crum et al. | 128/653 |
| 4,794,262 | A | 12/1988 | Sato et al. | 250/560 |
| 4,803,976 | A | 2/1989 | Frigg et al. | 128/92 |
| 4,821,200 | A | 4/1989 | Öberg | 364/474.24 |
| 4,821,206 | A | 4/1989 | Arora | 364/513 |
| 4,822,163 | A | 4/1989 | Schmidt | 356/1 |
| 4,825,091 | A | 4/1989 | Breyer et al. | 250/560 |
| 4,829,373 | A | 5/1989 | Leberl et al. | 358/88 |
| 4,835,710 | A | 5/1989 | Schnelle et al. | 364/513 |
| 4,836,778 | A | 6/1989 | Baumrind et al. | 433/69 |
| 4,841,967 | A | 6/1989 | Chang et al. | 128/303 |
| 4,869,247 | A | 9/1989 | Howard, III et al. | 128/303.1 |
| 4,875,478 | A | 10/1989 | Chen | 128/303 |
| 4,896,673 | A | 1/1990 | Rose et al. | 128/660.03 |
| 4,907,252 | A | 3/1990 | Aichinger et al. | 378/99 |
| 4,943,296 | A | 7/1990 | Funakubo et al. | 606/166 |
| 4,945,914 | A * | 8/1990 | Allen | 128/653 R |
| 4,955,891 | A | 9/1990 | Carol | 606/130 |
| 4,970,666 | A | 11/1990 | Welsh et al. | 364/522 |
| 4,987,488 | A | 1/1991 | Berci | 358/93 |
| 4,991,579 | A | 2/1991 | Allen | 128/653 |
| 5,016,639 | A | 5/1991 | Allen | 128/653 |
| 5,027,818 | A | 7/1991 | Bova et al. | 128/653 |
| 5,047,036 | A | 9/1991 | Koutrouvelis | 606/130 |
| 5,050,608 | A | 9/1991 | Watanabe et al. | 128/653 |
| 5,059,789 | A | 10/1991 | Salcudean | 250/206.1 |
| 5,078,140 | A | 1/1992 | Kwoh | 128/653.1 |
| 5,080,662 | A | 1/1992 | Paul | 606/130 |
| 5,086,401 | A | 2/1992 | Glassman et al. | 395/94 |
| 5,094,241 | A | 3/1992 | Allen | 128/653.1 |
| 5,097,839 | A | 3/1992 | Allen | 128/653.1 |
| 5,099,846 | A | 3/1992 | Hardy | 128/653.1 |
| 5,107,839 | A | 4/1992 | Houdek et al. | 128/653.1 |
| 5,119,817 | A | 6/1992 | Allen | 128/653.1 |
| 5,142,930 | A | 9/1992 | Allen et al. | 74/469 |
| 5,178,164 | A | 1/1993 | Allen | 128/898 |
| 5,186,174 | A | 2/1993 | Schlöndorff et al. | 128/653.1 |
| 5,197,476 | A | 3/1993 | Nowacki et al. | 128/660.03 |
| 5,198,877 | A | 3/1993 | Schulz | 356/375 |
| 5,207,223 | A | 5/1993 | Adler | 128/653.1 |
| 5,211,164 | A | 5/1993 | Allen | 128/653.1 |
| 5,211,165 | A | 5/1993 | Domoulin et al. | 128/653.1 |
| 5,230,338 | A | 7/1993 | Allen et al. | 128/653 |
| 5,230,623 | A | 7/1993 | Guthrie et al. | 433/72 |
| 5,249,581 | A * | 10/1993 | Horbal et al. | 128/664 |
| 5,251,127 | A | 10/1993 | Raab | 364/413.13 |
| 5,257,998 | A | 11/1993 | Ota et al. | 606/130 |
| 5,274,551 | A | 12/1993 | Corby, Jr. | 364/413.13 |
| 5,278,756 | A | 1/1994 | Lemchen et al. | 364/413.28 |
| 5,295,483 | A | 3/1994 | Nowacki et al. | 128/660.03 |
| 5,299,288 | A | 3/1994 | Glassman et al. | 395/80 |
| 5,300,080 | A | 4/1994 | Clayman et al. | 606/130 |
| 5,305,203 | A | 4/1994 | Raab | 364/413.13 |
| 5,309,913 | A | 5/1994 | Kormos et al. | 128/653.1 |
| 5,325,855 | A | 7/1994 | Daghighian et al. | 128/653.1 |
| 5,350,351 | A | 9/1994 | Saffer | 601/2 |
| 5,383,454 | A * | 1/1995 | Bucholz | 128/653.1 |
| 5,389,101 | A | 2/1995 | Heilbrun et al. | 606/130 |
| 5,394,457 | A * | 2/1995 | Leibinger et al. | 378/162 |
| 5,408,409 | A | 4/1995 | Glassman et al. | 364/413.13 |
| 5,445,166 | A | 8/1995 | Taylor | 128/897 |
| 5,479,597 | A | 12/1995 | Fellous | 395/154 |
| 5,483,961 | A | 1/1996 | Kelly et al. | 128/653.1 |
| 5,494,034 | A | 2/1996 | Schlöndorff et al. | 128/653.1 |
| 5,517,990 | A | 5/1996 | Kalfas et al. | 128/653.1 |
| 5,383,454 | A | 12/1996 | Bucholz | 128/653.1 |
| 5,588,430 | A | 12/1996 | Bova et al. | 128/653.1 |
| 5,617,857 | A | 4/1997 | Chader et al. | 128/653.1 |
| 5,622,170 | A | 4/1997 | Schulz | 128/653.1 |
| 5,630,431 | A | 5/1997 | Taylor | 128/897 |
| 5,631,973 | A | 5/1997 | Green | 382/128 |
| 5,662,111 | A | 9/1997 | Cosman | 128/653.1 |
| 5,676,673 | A | 10/1997 | Ferre et al. | 606/130 |
| 5,682,886 | A | 11/1997 | Delp et al. | 128/653.1 |
| 5,711,299 | A | 1/1998 | Manwaring et al. | 128/653.1 |
| 5,729,129 | A | 3/1998 | Acker | 324/207.12 |
| 5,732,703 | A | 3/1998 | Kalfas et al. | 128/653.2 |
| 5,735,278 | A | 4/1998 | Hoult et al. | 128/653.2 |
| 5,748,767 | A | 5/1998 | Raab | 382/128 |
| 5,755,725 | A | 5/1998 | Druais | 606/130 |
| RE35,816 | E | 6/1998 | Schulz | 356/376 |
| 5,769,078 | A | 6/1998 | Kliegis | 128/653.1 |
| 5,769,789 | A * | 6/1998 | Wang et al. | 600/414 |
| 5,769,861 | A | 6/1998 | Vilsmeier | 606/130 |
| 5,772,593 | A | 6/1998 | Hakamata | 600/407 |
| 5,795,294 | A | 8/1998 | Luber et al. | 600/407 |
| 5,799,099 | A | 8/1998 | Wang et al. | 382/131 |
| 5,800,352 | A | 9/1998 | Ferre et al. | 600/407 |
| 5,807,252 | A | 9/1998 | Hassfeld et al. | 600/407 |
| 5,810,008 | A | 9/1998 | Dekel et al. | 128/660.07 |
| 5,829,444 | A | 11/1998 | Ferre et al. | 128/897 |
| 5,848,967 | A | 12/1998 | Cosman | 600/426 |
| 5,880,976 | A | 3/1999 | DiGioia, III et al. | 364/578 |
| 5,995,738 | A | 11/1999 | DiGioia, III et al. | 395/500.32 |
| 6,002,859 | A | 12/1999 | DiGioia, III et al. | 395/500.32 |
| 6,011,987 | A * | 1/2000 | Barnett | 600/414 |
| 6,021,343 | A | 2/2000 | Foley et al. | 600/429 |
| 6,112,113 | A | 8/2000 | Van Der Brug et al. | 600/427 |
| 6,120,465 | A | 9/2000 | Gunthrie et al. | 600/587 |
| 6,122,341 | A | 9/2000 | Butler et al. | 378/20 |
| 6,135,946 | A | 10/2000 | Konen et al. | 600/117 |
| 6,149,592 | A | 11/2000 | Yanof et al. | 600/427 |
| 6,165,181 | A | 12/2000 | Heilbrun et al. | 606/130 |
| 6,167,145 | A | 12/2000 | Foley et al. | 382/128 |

| | | | | | | |
|---|---|---|---|---|---|---|
| 6,167,295 A | 12/2000 | Cosman ............... 600/426 | | 6,259,943 B1 | 7/2001 | Cosman et al. ......... 600/429 |
| 6,167,296 A | 12/2000 | Shahidi ............... 600/427 | | 6,275,725 B1 | 8/2001 | Cosman ............... 600/426 |
| 6,198,794 B1 | 3/2001 | Peshkin et al. ......... 378/42 | | 6,298,262 B1 | 10/2001 | Franck et al. ......... 600/426 |
| 6,205,411 B1 | 3/2001 | DiGioia, III et al. ..... 703/11 | | 6,341,231 B1 | 1/2002 | Ferre et al. ........... 600/424 |
| 6,216,029 B1 | 4/2001 | Paltieli ............... 600/427 | | 6,351,659 B1 | 2/2002 | Vilsmeier ............. 600/407 |
| 6,224,613 B1 | 5/2001 | Hofstetter ............ 606/130 | | 2001/0007919 A1 | 7/2001 | Shahidi ............... 600/427 |
| 6,226,548 B1 | 5/2001 | Foley et al. .......... 600/426 | | 2001/0027271 A1 | 10/2001 | Franck et al. ......... 600/426 |
| 6,236,875 B1 | 5/2001 | Bucholz et al. ........ 600/407 | | 2001/0039421 A1 | 11/2001 | Heilbrun et al. ....... 606/130 |
| 6,246,898 B1 | 6/2001 | Vesely et al. ......... 600/424 | | | | |
| 6,256,529 B1 | 7/2001 | Holupka et al. ........ 600/427 | | * cited by examiner | | |

…

FIDUCIAL MATCHING USING FIDUCIAL IMPLANTS

CROSS-REFERENCE TO RELATED APPLICATION

This application is a continuation of the U.S. National stage designation of co-pending International Patent Application No. PCT/CH98/00269, filed Jun. 22, 1998, the entire content of which is expressly incorporated herein by reference thereto.

FIELD OF THE INVENTION

The present invention relates to a device and method for referencing reference points of a fiducial implant.

BACKGROUND

In Computer Assisted Surgery ("CAS"), a computer tomogram comprising an image of a portion of a body, such as a bone, is generally used to assist the surgical intervention. For example, to determine the relative positions of a bone and one or more surgical instruments, the positions of the bone and surgical instrument in a coordinate system of the operating room can be compared with their positions as displayed in a computer tomogram.

To reduce soft tissue injury, minimally invasive surgical techniques involving CAS can be used to operate on bones, such as, for example, vertebrae, without exposing large bone surfaces. In CAS, a coordinate system corresponding to a patient in the operating room, as determined by a dynamic reference base of a position finding system, is registered with a coordinate system of a previously recorded tomographic image. This process, called matching involves a transformation between the coordinate systems.

A more comprehensive description of computer assisted surgery including a matching algorithm suitable for such coordinate transformations is given in L. P. Nolte et al, Clinical Evaluation of a System for Precision Enhancement in Spine Surgery, Clinical Biomechanics, 1995, Vol. 10, No. 6, PP 293–303, which is hereby incorporated by reference in its entirety.

One way to match the coordinate system of the patient in the operating room to the coordinate system of the image is to use mechanical scanning devices, such as those described in U.S. Pat. No. 5,383,454 to Buchholz. However, these known procedures are exceedingly time-consuming and presently only of obsolete accuracy.

German Application No. DE 29 704 393 to AESCULAP discloses a process for the preoperative determination of positioning data of endoprosthesis parts of a central joint relative to the bones that form the central joint. A device for determining the outer articulation point of a joint as the bones are displaced is also disclosed.

Another way of matching the patient's system of coordinates in the operating room with the image coordinate system consists of identifying predetermined points using anatomical reference points. Where the body parts are only partly exposed, however, this method is complicated by the restricted visual access. Frequently an endoscope must be used.

In another method to register the systems of coordinates, so-called fiducial implants are used to unequivocally identify the reference points. Such a method and appropriate apparatus are described in U.S. Pat. No. 4,945,914 to Allen. This method includes the implantation of at least 4 spatially related fiducial implants.

All these known methods share the drawback of being fairly time-consuming.

SUMMARY OF THE INVENTION

The present invention relates to a device for referencing reference points of a fiducial implant. The device preferably comprises at least one fiducial implant, such as a fiducial screw, suitable for insertion into a bone. The fiducial implant includes at least first and second reference points that have a known spatial relationship with respect to a head of the implant. The device also includes a pointer having a distal pointer end and at least three emitters or detectors that have a known spatial relationship with respect to the distal pointer end. Preferably, the emitters or detectors are arranged in a plane perpendicular to the longitudinal axis of the pointer. Each emitter or detector is configured to emit or detect radiation. The radiation preferably comprises electromagnetic radiation or acoustic waves. Preferably, the pointer includes emitters of electromagnetic radiation, such as light emitting diodes.

In one embodiment of the present invention, the pointer includes emitters and the device further includes a position finder comprising at least two detectors configured to detect the radiation emitted by the emitters of the pointer, whereby the positions of the emitters of the pointer and the pointer in three-dimensional space can be determined. Preferably, the detectors detect electromagnetic radiation or acoustic waves.

In another embodiment of the present invention, the pointer includes detectors and the device further includes a position finder comprising at least two emitters configured to emit radiation able to be detected by the detectors of the pointer, whereby the position of the detectors of the pointer and the pointer in three-dimensional space can be determined. Preferably, the emitters emit electromagnetic radiation or acoustic waves.

The head of the implant and the distal pointer end are preferably configured to removably and reproducibly mate to provide a known spatial relationship between the reference points and the distal pointer end to allow the position of each reference point in three dimensional space to be determined upon determining the position of the emitters or detectors of the pointer. The device of the present invention preferably includes a processor configured to perform a coordinate transformation to match the position of each reference point in three-dimensional space with a corresponding position of the respective reference point in a stored image of the bone.

In a preferred embodiment, the device comprises a second fiducial implant able to be inserted in a bone at a preferably spaced apart position from the first fiducial implant. The second fiducial implant is preferably configured with a head and reference points identical to the distal fiducial implant. The head of the second implant and the distal pointer end can preferably removably and reproducibly mate to provide a known spatial relationship between the reference points of the second fiducial and the distal pointer end to allow the positions of the reference points in three dimensional space to be determined.

In the preferred embodiment, the processor is configured to match the positions in three-dimensional space of the reference points of the second fiducial with the corresponding positions of the respective reference points in the stored image of the bone. The processor is also configured to perform a coordinate transformation between coordinates of points in three-dimensional space with the corresponding coordinates of the points in the stored image. Thus, the position of a selected point of the bone can be matched with the corresponding position of the selected point in the image of the bone and a selected point of an image of the bone can be matched with the corresponding point of the bone in physical space.

The head of the implant of the invention preferably comprises a cavity and the first end of the pointer preferably comprises a pin configured to be received within the cavity to provide the known spatial relationship between the reference points of the implant and the distal end of the pointer by means of the known dimensions of the implant and pointer and the reproducible mating between the implant and the pointer. Preferably, the distal end of the pointer comprises a shoulder adjoining the pin with the diameter of the shoulder being larger than the diameter of the pin. The shoulder is configured to abut the head of the implant when the pin is received within the cavity. Preferably, the pointer can be used to screw in or screw out the fiducial screw when the pin is received within the cavity.

Another embodiment of the invention comprises a method for creating a spatial relationship between reference points associated with a body. The method comprises inserting at least two fiducial implants in the body, each fiducial implant comprising at least two reference points. An image of the body showing at least two of the inserted fiducial implants is preferably obtained. The position in three-dimensional space of the reference points of at least two of the fiducial implants shown in the image is determined. A coordinate transformation is preferably performed to match the positions of the reference points in three-dimensional space with corresponding positions of the reference points in the image.

Preferably the step of determining the position of the reference points in three-dimensional space comprises mating a distal end of a pointer to a head of the implant and determining the position of the pointer using a position finder. Upon determining the position of the pointer, the position of the reference points can be found by means of the known dimensions of the implant and pointer and the reproducible mating between the implant and the pointer. The image is preferably a three-dimensional computer tomogram or an x-ray.

DETAILED DESCRIPTION OF THE PREFERRED EMBODIMENT

Figure 1:
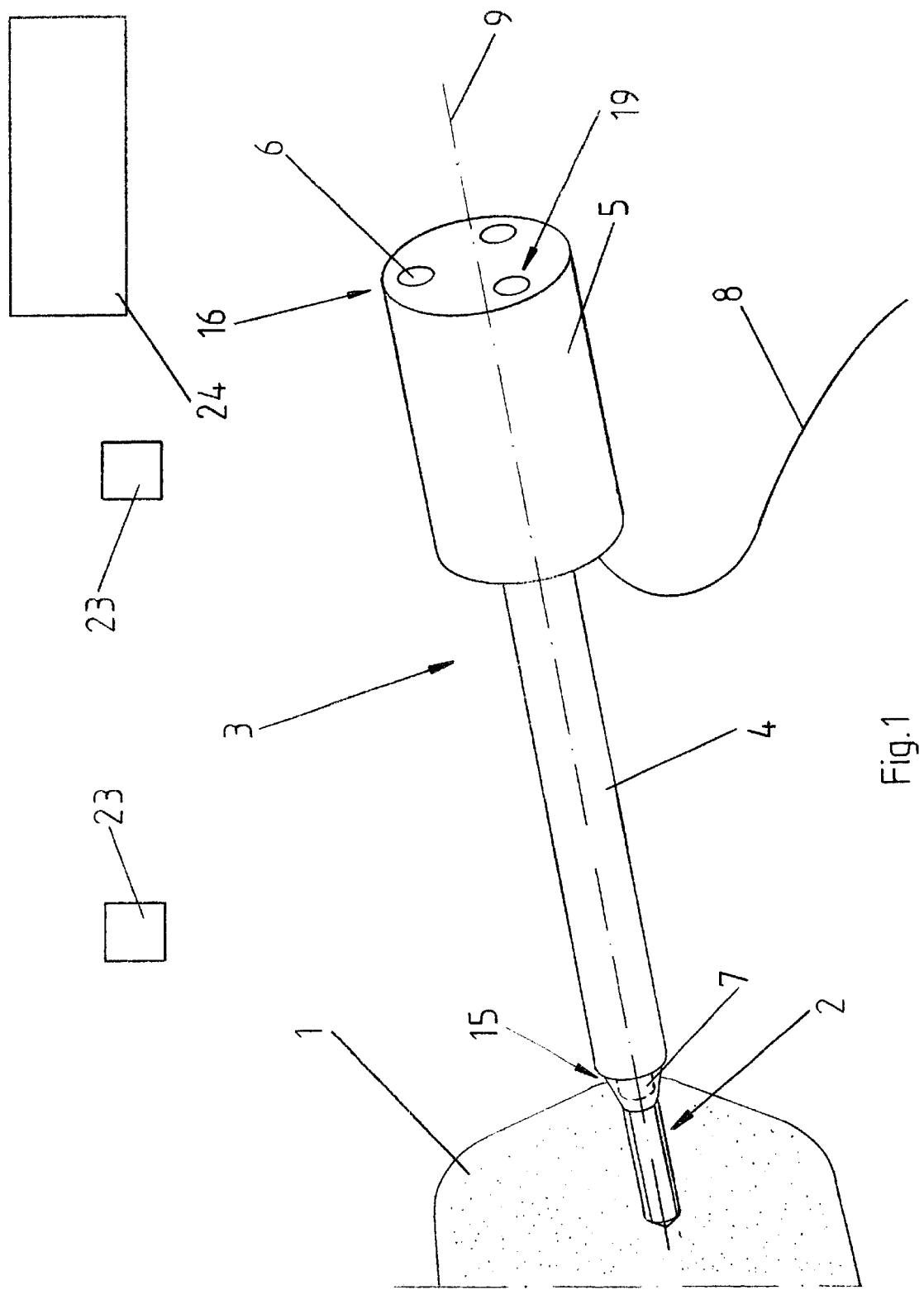
FIG. 1 is a perspective of an embodiment of the device of the invention.

The present invention relates to methods and apparatus for assisting surgical intervention. The invention allows a spatial relationship to be determined between reference points associated with the physical body's system of coordinates and the corresponding positions of the reference points in a coordinate system of an image of the body. Preferably, the body comprises at least a portion of a patient, such as a bone. The reference points associated with the body's system of coordinates are preferably reference points of at least one fiducial implant, such as a fiducial screw for insertion in a bone. Preferably two fiducial implants that each have two reference points are used so that only two implants are required to allow complete referencing of the coordinate systems. Thus, the present invention allows referencing of the coordinate systems while entailing minimal injury to the soft tissue around the site of intervention.

To reference the reference points, a pointer fitted with markers is positioned in a precisely defined spatial relationship relative a fiducial implant having fixed reference points. One reference point of the implant preferably corresponds to the tip of the implant and the other reference point preferably corresponds to the head of the implant. The implant head preferably includes a cavity which is concentric with the longitudinal axis of the implant. A distal end of the pointer preferably includes a pin, which is preferably concentric with the longitudinal axis of the pointer. The shapes of the cavity and pin are preferably complementary to one another so that the pin can be inserted into the cavity. Once the pin is received within the cavity, a portion of the pointer adjoining the pin, which has a larger diameter than the pin itself, preferably abuts the implant head adjacent the cavity. Accordingly the pointer and the fiducial implant are aligned along an axis defined by the implant reference points.

Using the markers of the pointer, the position of the pointer can be determined in three-dimensional space using a position detector, as described below. As used herein, determining the position of an object, such as a pointer or implant, includes determining its orientation. Thus, if the position of an object is known or determined, its orientation is also known or determined. Preferably the marker means include emitters/detectors that emit or detect electromagnetic or acoustic waves. The type of position detector depends on the type of marker means used, as discussed below.

Once the position of the marker means within a coordinate system is known, the position of the reference points of the fiducial implants can be determined based on the known dimensions of the pointer and of the fiducial implant. The pin preferably fits sufficiently securely within the cavity to provide a precise, reproducible spatial relationship between the pointer and the reference points.

The device and method for determining a spatial relation between reference points is based on the concept that a fiducial implant, such as a fiducial screw implanted in bone, can be visualized in an image, such as a three-dimensional computer tomogram or x-ray, of at least a portion of a body. Subsequently, the positions of the references points in the image can be determined in a coordinate system of the image. The present invention allows the positions of the reference points to be determined with respect to a three-dimensional coordinate system of the body having the implants.

Upon associating the positions of the reference points in the image with the positions of the reference points in the coordinate system of the body, any point in the image can be related by a coordinate transformation to the corresponding point in the physical body, and vice-versa. Fiduciary matching or registration thus relates to the determination of the spatial relationship of reference points in the coordinate system of the image to the reference point positions in the coordinate system of the physical body. Because the fiducial implant of the invention comprises at least two reference points, two fiducial implants inserted in the body provide a sufficient number of reference points to allow the registration or matching of the systems of the two coordinate systems. Thus, only the portion of the body receiving the implant need be exposed allowing for a minimally invasive registration of the coordinate systems.

Figure 2:
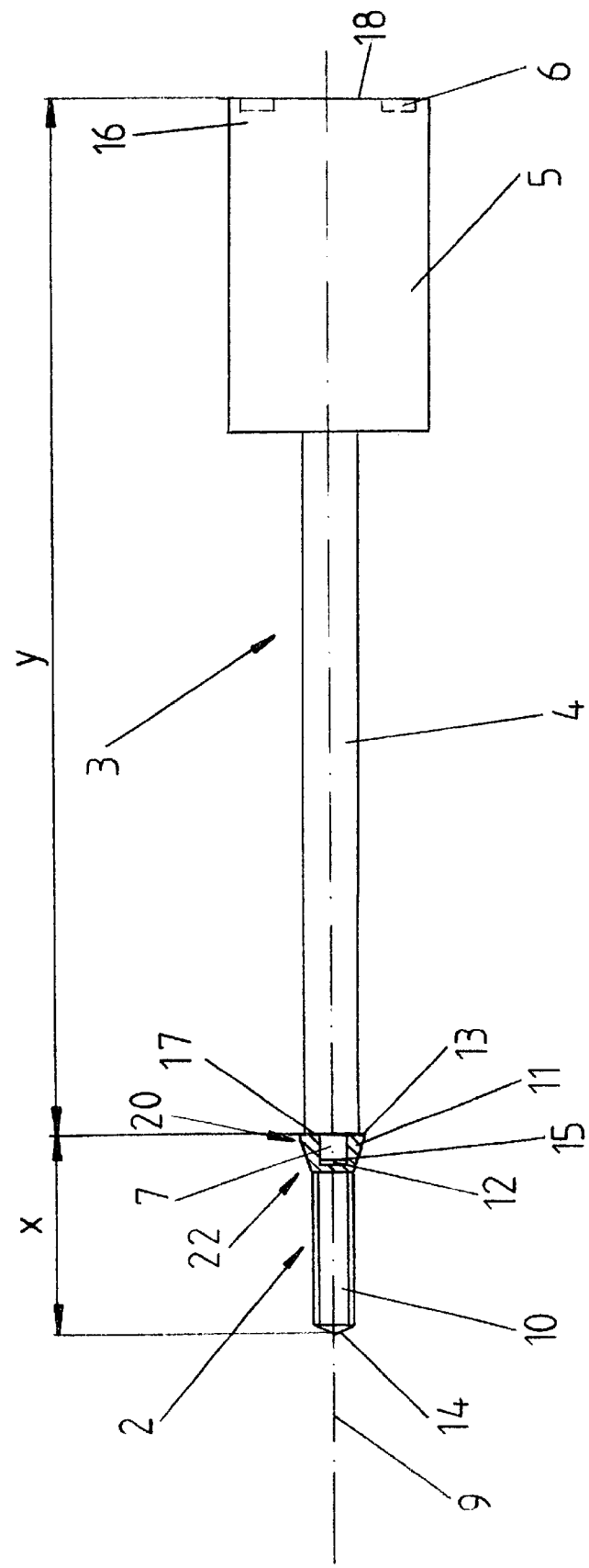
FIG. 2 is a partly sectional side view of an embodiment of the device of the invention.

The embodiment of the device of the invention shown in FIGS. 1 and 2 comprises at least one fiducial implant, such as a fiducial screw 2, having a longitudinal axis 9, a head 22, and distal tip 14. A distance (x) between distal tip 14 and head 22 of fiducial screw 2 is known precisely. Head 22 includes an aperture or cavity 12, which is preferably concentric with longitudinal axis 9. Cavity 12 is preferably cylindrical and can be configured with internal threads. Alternatively, cavity 12 can comprise other shapes, such as a hexagon or other polygon, suitable for receiving a drive tool to screw in or out fiducial screw 2.

The device of the invention also includes a pointer 3 having a distal end 15, a proximal end 16, a cylindrical stem 4, and a grip 5. Distal end 15, which is opposite grip 5, preferably includes a pin 7, which is preferably complementary in shape to cavity 12 allowing pin 7 to be concentrically and snugly inserted into cavity 12. Pin 7 is preferably cylindrical and can include external threads to provide a threaded engagement with cavity 12, whereby a rigid, detachable connection is be formed between the pointer 3 and the fiducial screw 2.

Pointer 3 preferably includes markers to allow the position of pointer 3 to be determined in three dimensional space. Preferably, the pointer includes at least three markers, which emit or detect electromagnetic radiation. Preferably, the markers are light emitting diodes (LED's) 6. Alternatively, the markers can be ultrasound transducers that emit or detect acoustic waves. Because diodes 6 are not collinear with one another, they define a plane 18, which is preferably oriented perpendicular to the longitudinal axis 9 of pointer 3. Diodes 6 and plane 18 are preferably disposed at rear end 16 of pointer 3.

The diameter of pin 7 is smaller than the diameter of the adjacent portion of stem 4. Therefore, when pin 7 is received within cavity 12, a shoulder of pointer 3 abuts or rests against a proximal portion 13 of fiducial screw 2. Preferably, proximal portion 13 of fiducial screw 2 and shoulder 17 are perpendicular to longitudinal axis 9 of the fiducial screw 2. Because of the cooperation between pin 7 and cavity 12 and between shoulder 17 and proximal portion 13 of the screw 2, the longitudinal axes of pointer 3 and fiducial screw 2 are coaxial when pin 7 is received within cavity 12. Therefore, the position and orientation of pointer 3 and screw 2 are defined with respect to one another.

A distance y between shoulder 17 and plane 18 of pointer 3 is known precisely. Because distance x of fiducial screw 2 and distance y of pointer 3 are known precisely and because screw 2 and pointer 3 are coaxially and concentrically aligned when pin 7 is received within cavity 12, the positions of distal tip 14 and head 22 are known precisely with respect to LED's 6. Therefore, if the position of LED's 6 are determined with respect to a given system of coordinates, such as a three-dimensional system of coordinates within a room, the positions of distal tip 14 and head 22 can be determined with respect to the same system of coordinates. Thus, distal tip 14 and head 22 of screw 2 comprise reference points, the positions of which can be determined precisely in three-dimensional space.

A position finder 24, which is preferably placed inside the room, can be used to determine and track the position of LED's 6 in three-dimensional space. Position finder 24 preferably includes at least two sensors 23 to detect the electromagnetic or acoustic waves emitted by the position determining means. Alternatively, the position finder may include emitters, to emit electromagnetic radiation or acoustic waves, suitable for detection by emitters associated with the pointer. In either case, the cooperation between the position finder and the markers of the pointer allow the position of the pointer in three-dimensional space to be determined. The position finder can be part of a CAS system and may include an image processing computer software. A suitable optical position finder includes one marketed under the name OPTOTRAK, Northern Digital Inc., Ontario, Canada.

A fiducial screw 2, which has been implanted into a bone 1, can be referenced to determine the positions in three dimensional space of the reference points defined by distal tip 14 and head 22. The referencing includes mating distal end 15 of pointer 3 with a fiducial implant to removably and reproducibly provide a known spatial relationship between the reference points and the distal end 15. The mating preferably includes inserting pin 7 into cavity 12 to provide a coaxial relationship between the fiducial implant and the pointer 3. In the preferred embodiment, upon mating the implant and the pointer, electromagnetic radiation emitted by LED's 6 of pointer 3 is detected to determine the position of the emitters in three-dimensional space. Because the spatial relationship between the emitters and pointer 3 are known, the position of the pointer in three dimensional space can determined. Because the spatial relationship between each reference point and proximal pointer end 15 is known when pointer 3 and the fiducial implant 2 are mated, the three-dimensional position of each reference point can be found from the position of the emitters.

The steps of mating and position determining can be repeated for each of the fiducial implants to be referenced. Subsequently, the positions of the reference points can be registered or matched with the corresponding coordinates of the reference points in an image showing the reference points. Suitable images can be recorded prior to the position determining and include, for example, 3-dimensional images formed by computer tomography. If the positions of the reference points of at least two implanted fiducial implants are matched with the corresponding positions of the reference points in an image of the body showing the implants, a coordinate transformation can be determined to allow the positions of points of the body and the corresponding positions of the body points in the image to be related to one another.

As an alternative to using a pointer configured with LED's emitting electromagnetic radiation, pointer 3 may be configured with markers to detect electromagnetic radiation or with acoustic transducers to emit or detect acoustic waves. In each of the alternative cases a position finder cooperates with the markers or acoustic transducers to allow the position of the pointer in three-dimensional space to be determined.

Although preferred embodiments of the invention have been illustrated in the foregoing description, it will be understood that the invention is not limited to the embodiments disclosed, but is capable of numerous rearrangements and modifications of parts and elements without departing from the spirit of the invention.

What is claimed is:

1. A device for referencing a fiducial implant, comprising:
    a fiducial implant for insertion into a portion of a body, the implant having first and second spaced apart reference points and a head, the head and the reference points having a known spatial relationship;
    a pointer having a distal pointer end and at least three emitters configured to emit radiation, the distal pointer end and the at least three emitters having a known spatial relationship;
    a position finder comprising at least two detectors configured to detect the radiation whereby the position of the at least three emitters in three-dimensional space can be determined; and wherein the head of the implant and the distal pointer end are configured to removably and reproducibly mate to provide a known spatial relationship between the first and second spaced apart reference points of the fiducial implant and the distal pointer end to allow the position of the first and second spaced apart reference points in three dimensional space to be determined.

2. The device of claim 1, wherein the body is a bone, and further comprising a processor configured to perform a coordinate transformation to match the position of each reference point in three-dimensional space with a corresponding position of the respective reference point in a stored image of the bone.

3. The device of claim 2, further comprising at least a second fiducial implant for insertion in the bone, the second implant having a head and at least third and fourth reference points, wherein the head of the second implant and the distal pointer end are configured to removably and reproducibly mate to provide a known spatial relationship between the third and fourth reference points and the distal pointer end to allow the position of the third and fourth reference points in three dimensional space to be determined.

4. The device of claim 3, wherein the processor is configured to match the positions in three-dimensional space of the third and fourth reference points with the positions of the respective reference points in the stored image of the bone and further wherein the processor is configured to perform a coordinate transformation whereby the position of a selected point on the bone can be matched with the corresponding position of the selected point in the image of the bone.

5. The device of claim 1, wherein the head of the fiducial implant comprises a cavity and the distal pointer end of the pointer comprises a pin configured to be received within the cavity to provide the known spatial relationship between the reference points and the first end of the pointer.

6. The device of claim 5, wherein the distal pointer end of the pointer comprises a shoulder adjoining the pin, the shoulder having a diameter larger than a diameter of the pin and being configured to abut the head of the implant when the pin is received within the cavity.

7. The device of claim 6, wherein the fiducial implant is a fiducial screw and the pointer can be used to screw in or screw out the fiducial screw when the pin is received within the cavity.

8. The device of claim 1, wherein the radiation comprises electromagnetic radiation or acoustic waves.

9. The device of claim 1, wherein the fiducial implant and pointer are arranged along a longitudinal axis and the at least three emitters are arranged in a plane perpendicular the longitudinal axis.

10. A method for determining a spatial relationship between reference points associated with a body, comprising:
    inserting at least two fiducial implants in the body, each fiducial implant providing at least two spaced apart reference points; and
    determining the position in three-dimensional space of the at least two spaced apart reference points of each of the at least two fiducial implants and determining the spatial relationship between the spaced apart reference points of the at least two fiducial implants.

11. The method of claim 10, wherein the body is a bone.

12. The method of claim 11, further comprising obtaining at least one image showing the bone and at least two of the inserted fiducial implants.

13. The method of claim 12, further comprising performing a coordinate transformation to match the positions of the reference points in three-dimensional space with corresponding positions of the reference points in the image.

14. The method of claim 10, wherein the step of determining the position comprises:
    providing a pointer having a distal end and at least three emitters configured to emit radiation, the distal end and the at least three emitters having a known spatial relationship;
    associating the distal end with one of the fiducial implants to removably and reproducibly provide a known spatial relationship between the reference points and the distal end;
    detecting the radiation to determine the position of the at least three emitters in three-dimensional space to allow the position of each reference point in three dimensional space to be determined; and
    repeating the associating step for each of the fiducial implants to be referenced.

15. The method of claim 10, wherein the image is a digitally recorded computer three-dimensional computer tomogram.

16. A method for determining a spatial relationship between reference points associated with a body, comprising:
    inserting at least one fiducial implant into the body, the fiducial implant having at least two spaced apart reference points;
    associating with the fiducial implant a pointer having at least three emitters configured to emit radiation, wherein the at least three emitters have a known spatial relationship and the fiducial implant and pointer are oriented along a longitudinal axis; and
    determining the position in three-dimensional space of the at least two spaced apart reference points of the implant associated with the pointer.

17. The method of claim 16, wherein the pointer has a distal end and the method comprises:
    associating the distal end with one of the fiducial implants to removably and reproducibly provide a known spatial relationship between the spaced apart reference points of the implant associated with the distal end and the distal end;
    detecting the radiation to determine the position of the at least three emitters in three-dimensional space to allow the position of each spaced apart reference point of the implant associated with the distal end to be determined in three dimensional space; and
    repeating the associating step for each of the fiducial implants to be referenced.

18. The method of claim 16, wherein the body is a bone.

19. The method of claim 18, further comprising obtaining at least one image showing the bone and at least two of the inserted fiducial implants.

20. The method of claim 19, further comprising performing a coordinate transformation to match the positions of the reference points in three-dimensional space with corresponding positions of the reference points in the image.

21. The device of claim 1, wherein the head of the fiducial implant is one of the first and second spaced apart reference points of the fiducial implant.

22. A device for referencing a fiducial implant for insertion into a portion of a body, the implant having first and second spaced apart reference points and a head, the head and the reference points having a known spatial relationship, the device comprising:

a pointer having a distal pointer end and at least three emitters configured to emit radiation, the distal pointer end and the at least three emitters having a known spatial relationship;

a position finder comprising at least two detectors configured to detect the radiation whereby the position of the at least three emitters in three-dimensional space can be determined; and wherein the head of the implant and the distal pointer end are configured to removably and reproducibly mate to provide a known spatial relationship between the first and second spaced apart reference points of the fiducial implant and the distal pointer end to allow the position of the first and second spaced apart reference points in three dimensional space to be determined.

23. The device of claim 22, wherein the implant is a screw configured to be screwed into a bone.

24. The method of claim 11, wherein at least one of the fiducial implants is a screw and the step of inserting comprises screwing the at least one screw into the bone.

25. The method of claim 16, wherein the body is a bone and at least one of the fiducial implants is a screw and the step of inserting comprises screwing the at least one screw into the bone.

* * * * *